United States Patent
Winfield et al.

(10) Patent No.: US 9,953,416 B2
(45) Date of Patent: Apr. 24, 2018

(54) PORTAL DOSIMETRY SYSTEM

(71) Applicant: ELEKTA AB (PUBL), Stockholm (SE)

(72) Inventors: Colin Winfield, Crawley (GB); Abdul Sayeed, Surrey (GB)

(73) Assignee: Elekta AB (PUBL), Stockholm (SE)

(*) Notice: Subject to any disclaimer, the term of this patent is extended or adjusted under 35 U.S.C. 154(b) by 41 days.

(21) Appl. No.: 14/992,117

(22) Filed: Jan. 11, 2016

(65) Prior Publication Data

US 2016/0125602 A1    May 5, 2016

Related U.S. Application Data (63) Continuation of application No. 13/927,391, filed on Jun. 26, 2013, now Pat. No. 9,269,137.

(51) Int. Cl.
     *G06T 7/00*      (2017.01)
     *G06K 9/62*      (2006.01)
     (Continued)

(52) U.S. Cl.
     CPC .......... *G06T 7/0012* (2013.01); *A61N 5/1071* (2013.01); *G06F 17/30259* (2013.01);
     (Continued)

(58) Field of Classification Search
None
See application file for complete search history.

(56) References Cited

U.S. PATENT DOCUMENTS

2007/0041497 A1*   2/2007   Schnarr .................. A61N 5/103
                                                       378/65
2007/0081629 A1*   4/2007   Yin ....................... A61N 5/1031
                                                       378/65
(Continued)

FOREIGN PATENT DOCUMENTS

CN          1953782        4/2007
CN        101184526        5/2008
(Continued)

OTHER PUBLICATIONS

Nijsten et al., "Routine individualised patient dosimetry using electronic portal imaging devices," Radiotherapy and Oncology, vol. 83, 2007, pp. 65-75.*
(Continued)

*Primary Examiner* — Matthew Bella
*Assistant Examiner* — Soo Shin
(74) *Attorney, Agent, or Firm* — Finnegan, Henderson, Farabow, Garrett & Dunner LLP (57) ABSTRACT

Embodiments of the invention provide systems and methods for evaluating treatment parameters for a patient undergoing radiotherapy. The method includes the step of generating a portal dosimetry image showing differences between a planning image obtained prior to a treatment session and a portal image obtained during the treatment session. A database of prior portal dosimetry results is accessed, and a processor is used to perform a similarity measurement between the portal dosimetry image and the prior portal dosimetry results. Based on the similarity measurement, the system determines whether radiation was delivered as planned during the treatment session.

25 Claims, 4 Drawing Sheets

(51) Int. Cl.
| | |
|---|---|
| *G06F 17/30* | (2006.01) |
| *G06F 19/00* | (2011.01) |
| *A61N 5/10* | (2006.01) |

(52) U.S. Cl.
CPC ........ *G06F 19/321* (2013.01); *G06F 19/3481* (2013.01); *G06K 9/6202* (2013.01); *G16H 50/20* (2018.01); *A61N 2005/1054* (2013.01); *G06T 2207/10004* (2013.01); *G06T 2207/10116* (2013.01)

(56) References Cited

U.S. PATENT DOCUMENTS

| | | | |
|---|---|---|---|
| 2008/0031406 A1* | 2/2008 | Yan | A61N 5/1037 378/14 |
| 2009/0067576 A1* | 3/2009 | Maltz | A61N 5/1048 378/65 |
| 2010/0012829 A1* | 1/2010 | Islam | A61N 5/1048 250/252.1 |
| 2010/0027763 A1 | 2/2010 | Carlsson | |
| 2010/0119032 A1* | 5/2010 | Yan | A61N 5/1049 378/4 |
| 2012/0250971 A1* | 10/2012 | Holmes | A61N 5/1048 382/132 |
| 2013/0085798 A1* | 4/2013 | Spatola | G06Q 10/06 705/7.24 |
| 2013/0090549 A1 | 4/2013 | Meltsner et al. | |
| 2014/0105355 A1* | 4/2014 | Toimela | A61N 5/103 378/41 |

FOREIGN PATENT DOCUMENTS

| | | |
|---|---|---|
| WO | WO 2013/119887 A1 | 8/2013 |
| WO | WO 2014/056831 A1 | 4/2014 |

OTHER PUBLICATIONS

International Search Report, issued from the European Patent Office, in corresponding Application No. PCT/IB2014/062498, dated Sep. 30, 2014, 12 pages.

P. Vial, P. Hunt, P.B. Greer, L. Oliver, and C. Baldock, "Software tool for portal dosimetry research," Australasian Physical & Engineering Sciences in Medicine, vol. 31, No. 3, 2008, pp. 216-222.

J.J. Gordon and J.V. Siebers, WO 2013/119887 A1, PCT/US2013/025245, filed Feb. 8, 2013.

International Preliminary Report on Patentability issued by the International Bureau in corresponding Application No. PCT/IB2014/062498, dated Jan. 7, 2016, 7 pages.

International Search Report, issued from the European Patent Office, in corresponding European Application No. 14734235.6-1666, dated Jun. 21, 2016, 4 pp.

Persoon et al., "Interfractional trend analysis of dose difference based on 2D transit portal dosimetry." Phys. Med. Biol., vol. 57, No. 20, Sep. 21, 2012, pp. 6445-6458.

Notification of the First Office Action from the State Intellectual Property Office of the People's Republic of China in application No. 201480042565.4, dated Dec. 5, 2017.

* cited by examiner

PORTAL DOSIMETRY SYSTEM

CROSS REFERENCES TO RELATED APPLICATIONS

This application is a continuation of U.S. patent application Ser. No. 13/927,391 filed Jun. 26, 2013, entitled "PORTAL DOSIMETRY SYSTEM." The disclosure of the above-referenced application is expressly incorporated herein by reference in its entirety.

TECHNICAL FIELD

This invention relates to systems and methods for radiation therapy and, in particular, to systems and methods for comparing a planned radiation treatment session with an actual radiation treatment session.

BACKGROUND

Portal dosimetry is a technique used in radiation therapy for comparing a planned radiation dose with an actual or delivered radiation dose. Prior to a treatment session (i.e., during a planning phase), a planning image of a treatment area within a patient is generated. The planning image represents a prediction of a portal image that will be obtained during the treatment session. When the actual portal image has been obtained, the planning image and the portal image are compared to identify any differences between the two images. Such differences may be characterized as being either true positive differences or false positive differences. A true positive difference occurs when the radiation dose was not delivered as intended, and adjustments to a treatment plan are likely required. On the other hand, a false positive difference occurs when the radiation dose was delivered as intended, and adjustments to the treatment plan are probably not required.

Unfortunately, due to the large number of variables involved in generating and interpreting the planning images and the portal images, it can be difficult and/or time consuming for a physicist or other user of a portal dosimetry system to distinguish between true positive differences and false positive differences. For example, a gas bubble within the patient may cause a false positive difference, but the physicist may have difficulty recognizing the gas bubble and that the radiation was likely delivered as planned. Likewise, it may be difficult for the physicist to distinguish between a true positive difference caused by displacement of the patient and a false positive difference caused by displacement of an imaging device. Such analyses can take considerable time and incur significant expense.

There is a need for improved systems and methods for interpreting portal dosimetry results. In particular, needs exist for systems and methods that allow physicists to distinguish between true positive differences and false positive differences.

SUMMARY OF THE INVENTION

In certain embodiments, an expert decision system is provided to assist physicists with interpretation and analysis of portal dosimetry results and images. The system includes a database of previously analyzed portal dosimetry images, classified according to disease, plan type, treatment devices, treatment region, and other patient and/or treatment characteristics. The database also stores portal dosimetry analysis results for the images, including information about any true positive differences or false positive differences associated with the images, and any corresponding decisions made by a physicist regarding the images. Accordingly, when a new portal dosimetry image is being analyzed by a physicist, the system may access the database and perform a similarity measurement between the new portal dosimetry image and the prior portal dosimetry images in the database. The system may then provide the physicist with a ranked list of likely explanations for any differences seen in the new portal dosimetry image. Additionally or alternatively, the system may help the physicist characterize differences in the new portal dosimetry image as being either true positive differences or false positive differences.

In one aspect, the invention relates to a method of evaluating treatment parameters for a patient undergoing radiotherapy. The method includes: (a) obtaining a planning image of the patient prior to a radiotherapy treatment session; (b) obtaining a portal image during the radiotherapy treatment session; (c) generating a portal dosimetry image showing a difference between the planning image and the portal image; (d) accessing a database having prior portal dosimetry images and corresponding assessments of the prior portal dosimetry images; (e) using a processor, performing a similarity measurement between the portal dosimetry image and the prior portal dosimetry images; and (e) based on the similarity measurement and the assessments of the prior portal dosimetry images, providing an indication that the difference between the planning image and the portal image is either a true positive difference or a false positive difference. The true positive difference indicates that radiation was not delivered as planned during the radiotherapy treatment session. The false positive difference indicates that radiation was delivered as planned during the radiotherapy treatment session. Both the planning image and the portal image correspond to a target region of the patient.

In certain embodiments, the planning image depicts a predicted portal image for the radiotherapy treatment session. The planning image and/or the portal image may include or be a 3D image. In one embodiment, the generating step includes calculating a gamma index. The database may include prior planning images and prior portal images used to generate the prior portal dosimetry images. The prior portal dosimetry images may include images of the target region of the patient. In one embodiment, performing the similarity measurement includes calculating a dice coefficient.

In various embodiments, providing an indication includes providing a list of possible causes for the difference between the planning image and the portal image. In some embodiments, providing an indication includes providing further information, which may include: (i) displaying one or more of the prior portal dosimetry images, (ii) recommending a consultation with a colleague, and/or (iii) recommending that an additional image of the patient be obtained. The false positive difference may be due to, for example, a gas bubble, a displaced portal imaging panel, and/or a patient coughing spasm. The true positive difference may be due to, for example, movement of patient anatomy, a treatment plan selection fault, improper aperture size, and/or improper aperture shape.

In another aspect, the invention relates to a system for evaluating treatment parameters for a patient undergoing radiotherapy. The system includes a register for storing: (i) a planning image corresponding to a target region of the patient; (ii) a portal image corresponding to the target region of the patient; and (iii) prior portal dosimetry images and corresponding assessments of the prior portal dosimetry images. The planning image is obtained prior to a radiotherapy treatment session, and the portal image is obtained during the radiotherapy treatment session. The system also includes a processor configured to: (i) generate a portal dosimetry image showing a difference between the planning image and the portal image; (ii) perform a similarity measurement between the portal dosimetry image and the prior portal dosimetry images; and (iii) based on the similarity measurement and the assessments of the prior portal dosimetry images, provide an indication that the difference between the planning image and the portal image is either a true positive difference or a false positive difference. The true positive difference indicates that radiation was not delivered as planned during the radiotherapy treatment session. The false positive difference indicates that radiation was delivered as planned during the radiotherapy treatment session.

In certain embodiments, the planning image depicts a predicted portal image for the radiotherapy treatment session. The planning image and/or the portal image may include or be a 3D image. In one embodiment, the processor is configured to calculate a gamma index for the generation of the portal dosimetry image. The register may be for storing prior images and prior portal images used to generate the prior portal dosimetry images. The prior portal dosimetry images may include images of the target region of the patient. In some embodiments, the processor is configured to calculate a dice coefficient for the similarity measurement.

In various embodiments, the indication includes or is a list of possible causes for the difference between the planning image and the portal image. The processor may be configured to provide further information such as (i) one or more of the prior portal dosimetry images, (ii) a recommendation to consult with a colleague, and/or (iii) a recommendation to obtain an additional image of the patient. The false positive difference may be due to, for example, a gas bubble, a displaced portal imaging panel, and/or a patient coughing spasm. The positive difference may be due to, for example, movement of patient anatomy, a treatment plan selection fault, improper aperture size, and/or improper aperture shape.

The foregoing and other objects, features and advantages of the present invention disclosed herein, as well as the invention itself, will be more fully understood from the following description of preferred embodiments and claims, when read together with the accompanying drawings. In the drawings, like reference characters generally refer to the same parts throughout the different views. The drawings are not necessarily to scale, emphasis instead generally being placed upon illustrating the principles of the invention.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

While the invention is particularly shown and described herein with reference to specific examples and specific embodiments, it should be understood by those skilled in the art that various changes in form and detail may be made therein without departing from the spirit and scope of the invention.

DETAILED DESCRIPTION

It is contemplated that devices, systems, methods, and processes of the claimed invention encompass variations and adaptations developed using information from the embodiments described herein. Adaptation and/or modification of the devices, systems, methods, and processes described herein may be performed by those of ordinary skill in the relevant art.

Throughout the description, where devices and systems are described as having, including, or comprising specific components, or where processes and methods are described as having, including, or comprising specific steps, it is contemplated that, additionally, there are devices and systems of the present invention that consist essentially of, or consist of, the recited components, and that there are processes and methods according to the present invention that consist essentially of, or consist of, the recited processing steps.

It should be understood that the order of steps or order for performing certain actions is immaterial so long as the invention remains operable. Moreover, two or more steps or actions may be conducted simultaneously.

Typical portal dosimetry analysis identifies differences between a planned radiation dose and a delivered radiation dose, based on images obtained before and during radiation treatment. As discussed above, however, analysis and interpretation of portal dosimetry results can take a significant amount of time, and conclusions by physicists are not always accurate.

In various embodiments, the systems and methods described herein assist a physicist with the interpretation of portal dosimetry results. The process starts by obtaining a planning image, prior to treatment, of the target area of the patient. The planning image may be a 3D image that includes a plurality of 2D images and may depict an anticipated or expected portal image. During the treatment session, portal images of the treatment area are obtained and may be used to reconstruct a 3D portal image of the target region at the time of treatment. In one example, treatment is interrupted if it appears that the dose is being delivered to the wrong location, or that the target has changed position substantially, based on the portal images.

In general, the systems and methods use the planning image and the portal image to determine whether the radiation dose was delivered to the patient as planned. In some implementations, differences between the planning image and the portal image are evaluated by computing a gamma index, which compares pixels in the planning image with corresponding pixels in the portal image. Differences between the two images (e.g., as indicated by the gamma index) may then be displayed in a portal dosimetry image, in which regions of high similarity are given one color or intensity, and regions of low similarity are given a different color or intensity. For example, if the target (e.g., a tumor) changes shape between the planning image and the portal image, the change in shape or size may appear as a highlighted region (e.g., in the color red) in the portal dosimetry image.

The portal dosimetry image may then be used to characterize differences between the planning image and the portal image as either true positive differences or false positive differences. A true positive difference occurs when the radiation dose was not delivered as intended, and adjustments to the treatment plan are likely required. True positive differences have many possible causes, including a change in tumor shape or location, a shift in patient position, or a broken multi-leaf collimator. On the other hand, a false positive difference occurs when the radiation dose was delivered as intended, and adjustments to the treatment plan are probably not required. False positive differences also have many possible causes, including the appearance or disappearance of a gas bubble in the patient, a displaced portal imaging panel, or other imaging inaccuracies.

Figure 1:
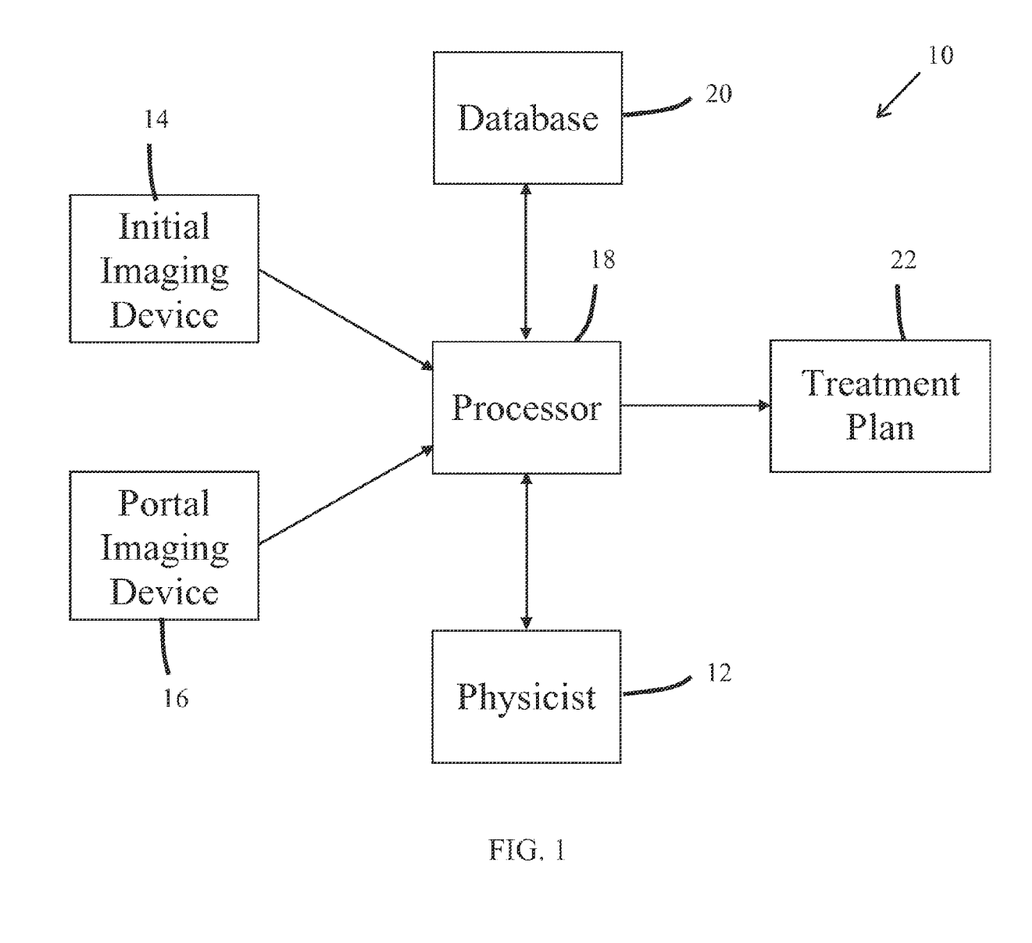
FIG. 1 is a schematic diagram of a system for analyzing portal dosimetry results, in accordance with certain embodiments of the invention.

Referring to FIG. 1, a system 10 is provided for assisting a physicist 12 with the interpretation of portal dosimetry results. The system 10 includes an initial imaging device 14 for obtaining or providing a planning image of the patient prior to a radiotherapy session. The planning image may represent or depict an anticipated portal image of the patient, to be obtained during the radiotherapy treatment session. The initial imaging device 14 may be any suitable imaging device that is capable of providing an image of the target region of the patient. Examples of suitable initial imaging devices include Computed Tomography (CT) scanners, Magnetic Resonance (MR) imagers, ultrasound imagers, and fluoroscopes or machines which are capable of producing X-ray, MR, or ultrasound images. In some embodiments, raw data is acquired from a CT scanner and a treatment planning system uses the raw data to calculate a radiation dose, which may then be used to calculate a gamma index.

The system 10 also includes a portal imaging device 16 for obtaining or providing a portal image of the patient during the radiotherapy session. The portal image may represent or depict an actual dose distribution that was delivered to the patient during the radiotherapy treatment session. The portal imaging device 16 may be any suitable imaging device that is capable of obtaining the portal image. An example of a suitable portal imaging device is iViewGT, manufactured by Elekta AB, of Sweden.

The system 10 also includes a processor 18 for receiving and comparing the planning image and the portal image. For example, the processor 18 may generate a portal dosimetry image that highlights differences between the planning image and the portal image. In some embodiments, the processor calculates and displays a gamma index in the portal dosimetry image. Information received and generated by the processor 18 is preferably displayed on a graphical display.

The system 10 also includes a database 20 of prior portal dosimetry images and assessments of the prior portal dosimetry images. The processor 18 accesses the information in the database 20 to analyze the difference between the planning image and the portal image, which may be presented in the portal dosimetry image. In some embodiments, the processor 18 accesses the prior portal dosimetry images and performs a similarity measurement between the portal dosimetry image and the prior portal dosimetry images. Based on the similarity measurement, the processor 18 may provide an indication (e.g., a computed probability) that the difference between the planning image and the portal image is either a true positive difference or a false positive difference. The physicist 12 and/or the processor 18 may use this indication to make one or more changes to a treatment plan 22, as needed.

In various embodiments, additional portal dosimetry results and images are added to the database 20 over time. For example, once a new portal dosimetry image has been analyzed, the image and a corresponding assessment of the image may be added to the database 20 for future reference. In this way, the database 20 of portal dosimetry results may become a larger and more accurate source of information, over time.

Figure 2:
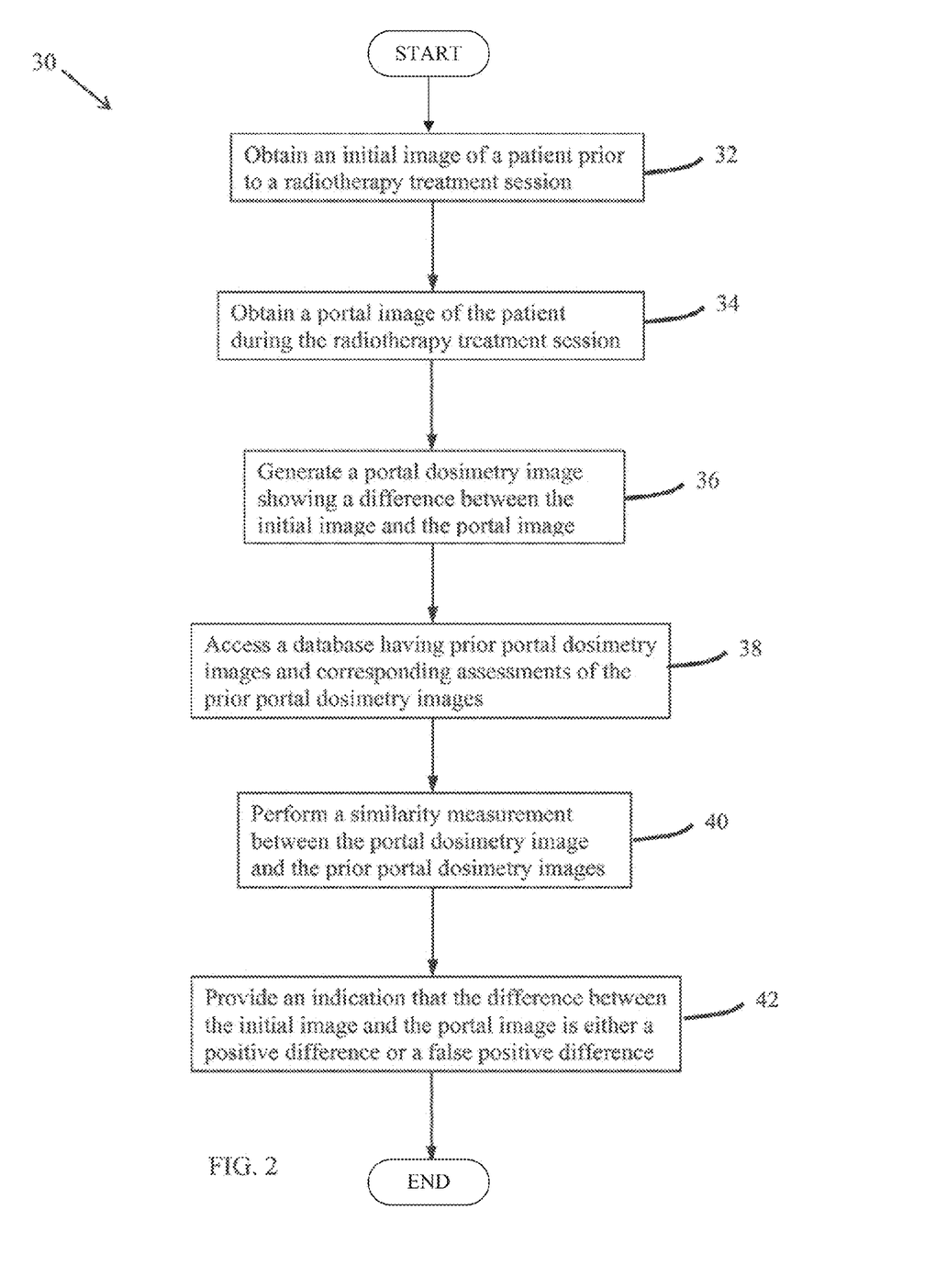
FIG. 2 is a flowchart of a method for analyzing portal dosimetry results, in accordance with certain embodiments of the invention.

FIG. 2 is a flowchart of a method 30 of evaluating treatment parameters for a patient undergoing radiotherapy, in accordance with certain embodiments of the invention. The method includes obtaining (step 32) a planning image of the patient prior to a radiation treatment session, using the initial imaging device 14. During the treatment session, a portal image of the patient is obtained (step 34), using the portal imaging device 16. The processor 18 is then used to generate (step 36) a portal dosimetry image that shows a difference between the planning image and the portal image. The processor accesses (step 38) the database 20 containing prior portal dosimetry images and assessments of the prior portal dosimetry images, which may be classified according to disease, plan type, treatment devices, treatment region, and other patient and/or treatment characteristics. The processor 18 is used to perform (step 40) a similarity measurement between the portal dosimetry image and the prior portal dosimetry images. The similarity measurement may be performed using a classifier technique, such as a fuzzy logic or a k-means clustering technique. The classifier technique may learn from data patterns and become more accurate as additional data is collected. Based on the similarity measurement, an indication is provided (step 42) that the difference between the planning image and the portal image is either a true positive difference or a false positive difference. For example, the processor 18 may generate a list of possible explanations for the difference.

Figure 3:
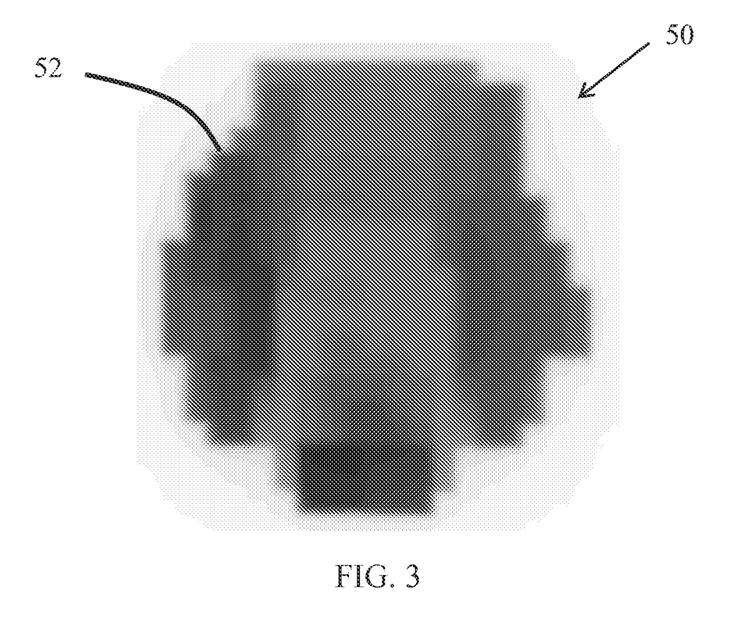
FIG. 3 is a portal image obtained during a radiotherapy treatment session, in accordance with certain embodiments of the invention.

FIG. 3 is an example of a portal image 50 obtained during a radiation treatment session, in accordance with certain embodiments of the invention. The portal image includes different colors and/or pixel intensities that represent different levels of radiation intensity and/or patient features, as seen from a portal imaging panel. A perimeter 52 of the portal image 50 corresponds to an edge of a radiation beam, as defined by, for example, a multi-collimator leaf system.

Figure 4:
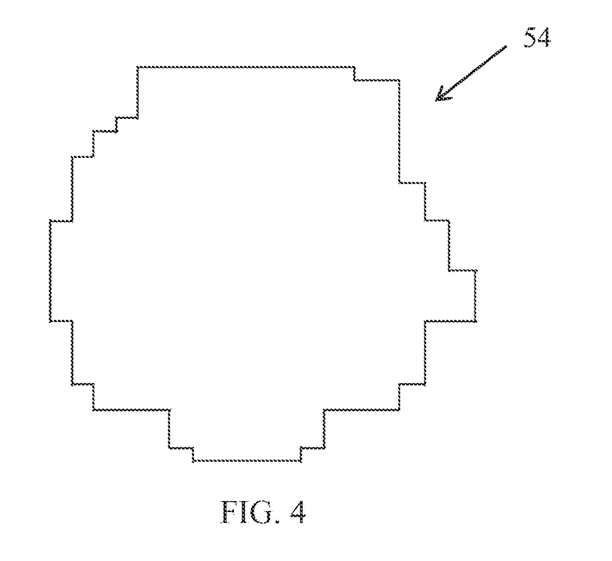
FIG. 4 is a schematic representation of a portal dosimetry image showing no differences between a planning image and a portal image, in accordance with certain embodiments of the invention.

In various embodiments, the systems and methods are used to generate a portal dosimetry image that shows one or more differences between a planning image and the portal image. The portal dosimetry image may highlight the differences using different colors and/or pixel intensities. Referring to FIG. 4, when no substantial differences exist, a portal dosimetry image 54 may be substantially uniform. By contrast, referring to FIGS. 5-8, when substantial differences exist, a portal dosimetry image may reveal these differences.

Figure 5:
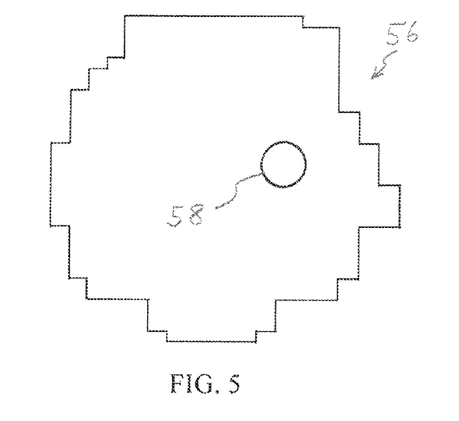
FIG. 5 is a schematic representation of a portal dosimetry image showing differences between a planning image and a portal image due to a gas bubble inside a patient, in accordance with certain embodiments of the invention.

For example, FIG. 5 is a schematic representation of a portal dosimetry image 56 showing a gas bubble 58, which was present in the portal image but not in the planning image. In general, one or more gas bubbles may appear within the patient during radiation therapy and typically do not adversely affect the delivery of radiation or require the treatment plan to be revised. Assuming the gas bubble 58 did not interfere with the radiation delivery, any differences attributed to the gas bubble 58 may be considered to be false positive differences.

Figure 6:
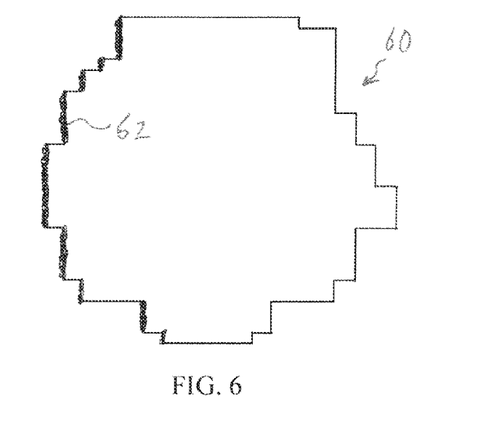
FIG. 6 is a schematic representation of a portal dosimetry image showing differences between a planning image and a portal image due to movement of a portal imaging panel, in accordance with certain embodiments of the invention.

Likewise, FIG. 6 is a schematic representation of a portal dosimetry image 60 showing the effects of a displaced portal imaging panel. In such an instance, features of the target region may still be visible through an aperture of multi-leaf collimator leaves, even if the features are not projected onto the panel in the expected positions. As depicted, when the panel is displaced, most of the differences between the planning image and the portal image may appear in the portal dosimetry image along one side 62 of the portal dosimetry image. Because a displaced portal imaging panel would likely not interfere with radiation delivery to the patient, such differences may be considered to be false positive differences.

Figure 7:
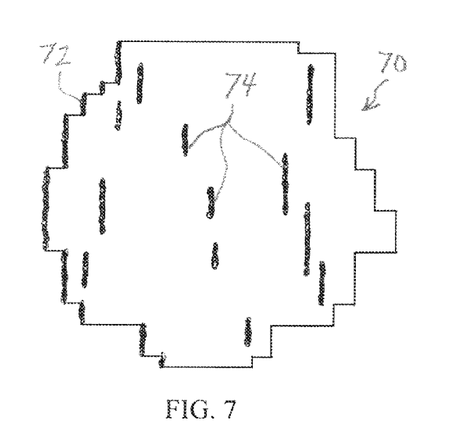
FIG. 7 is a schematic representation of a portal dosimetry image showing differences between a planning image and a portal image due to incorrect positioning of a patient during a treatment session, in accordance with certain embodiments of the invention.

FIG. 7 is a schematic representation of a portal dosimetry image 70 showing the effects of improper patient positioning during the radiotherapy treatment session. In this instance, the portal dosimetry image 70 may highlight differences in numerous locations, in the direction in which the patient was displaced. For example, the gamma index may show differences along an edge 72 of the portal dosimetry image 70 and along boundaries 74 associated with tissues having different densities. Such differences are likely true positive differences, because improper patient positioning would likely interfere with the delivery of radiation to the patient.

Figure 8:
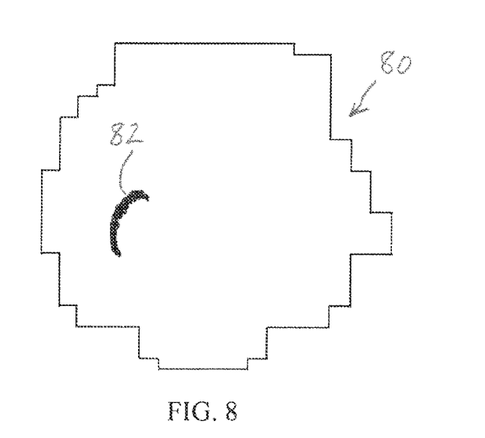
FIG. 8 is a schematic representation of a portal dosimetry image showing differences between a planning image and a portal image due to growth of a tumor, in accordance with certain embodiments of the invention.

As another example, FIG. 8 is a schematic representation of a portal dosimetry image 80 showing results obtained when a tumor or lesion has grown in the time between the planning image and the portal image. In such an instance, the additional growth of the lesion may appear in the portal dosimetry image as a crescent shape 82. This difference is likely a true positive difference, because radiation was likely not delivered to the tumor as planned.

In various embodiments, the systems and methods described herein facilitate the analysis and interpretation of portal dosimetry images and results by accessing a database of previous portal dosimetry results. For example, when interpreting new portal dosimetry images for a particular patient, the systems may review images for the same patient from previous, successful treatment sessions, and identify differences between the new images and the previous images. Alternatively or additionally, the system may compare the new and previous images using a rules-based analysis technique. In one implementation, the systems utilize a set of rules to determine the most likely cause of any difference between the new and previous images. For example, when treatment is for a prostate and an error in gamma index exceeds a certain value and is circular, the systems may use the set of rules to determine that the error was most likely caused by a gas bubble. In one embodiment, the system compares previous images from a successful treatment session with new portal dosimetry images to reveal a false positive, such as a gas bubble, in the new images.

In some embodiments, images from one successful set may be marked as "ok" and for a set that fails a gamma test, projections are compared at approximately the same angle. If some of the projections have a high dice coefficient (i.e., are similar in mutual information terms) and have a defined registration vector, but others in the treatment show a marked movement, the projections might indicate a coughing spasm. For example, when a patient coughs during treatment, significant differences may appear between the portal image and the planning image, due to movement of the patient. After the cough, the patient may not be in exactly the same position, which may cause additional differences between the images. The systems and methods may be used to recognize that a large global error in gamma index followed by a positioning error is indicative of a cough.

In some implementations, the systems and methods look at projections between sets and determine if all projections are sufficiently different, or if only some are different. Such results may indicate that something happened during a portion of the treatment (e.g., the patient moved, experienced bowel gas, etc.), or that something happened throughout the entire treatment (e.g., the patient was the wrong patient or in the wrong position, or the treatment plan was incorrect).

In various embodiments, a gamma test is performed in which a gamma index is calculated for two or more images. When the gamma index exceeds a threshold value, the gamma test may be considered to have been failed. For example, when pixel variation between the two images is greater than 3% within 3 mm of distance between the two or more images, the system may conclude that the gamma test has been failed.

Embodiments of the invention also provide techniques for comparing an exposed area for each projection against expected values, and identifying exposed areas that have apertures in different positions (e.g., specific leaves lagging or sticking, or a different prescription being delivered). These different aperture positions may occur throughout the treatment session or may occur intermittently. In some instances, a shift of anatomy in a digitally reconstructed radiograph (e.g., as indicated by the dice coefficient) may suggest that a wrong part of the patient's anatomy was or is being irradiated.

The systems and methods may also recognize when apertures are of different sizes, shapes, or orientations. Such instances may be caused by a machine or treatment plan selection fault, or it may be that a volume of the back-projected irradiated area was compared against the expected plan. The systems and methods may "learn" by analyzing dice coefficient values and/or aperture sizes per projection.

In certain embodiments, the systems and methods offer suggestions for causes of differences in portal dosimetry images, without necessarily doing a complete fault diagnostic analysis. The systems and methods may utilize many rules or tests in sequence and apply error margins. The error margins may be developed per anatomical site, as some portions of patients' bodies are less rigid or more malleable than other portions. A clustering analysis may be performed, using different regions of the gamma index as inputs. In one embodiment, a neural network is generated for all of the results (i.e., all gamma index values, etc.).

In various embodiments, the systems and methods gather more data for the physicist to analyze, based on the types of data that were requested by physicists on previous occasions when a similar problem presented itself. For example, the systems and methods may collect and present additional images, additional information about the patient, and/or make a request for re-examination.

Embodiments of the systems and methods described herein may be implemented as software running on a personal computer (e.g., a PC with an INTEL processor or an APPLE MACINTOSH) capable of running such operating systems as the MICROSOFT WINDOWS family of operating systems from Microsoft Corporation of Redmond, Wash., the MAC OS operating system from Apple Computer of Cupertino, Calif., and various varieties of Unix, such as SUN SOLARIS from SUN MICROSYSTEMS, and GNU/Linux from RED HAT, INC. of Durham, N.C. (and others). The systems and methods may also be implemented on such hardware devices as a smart or dumb terminal, a point of sale device (POS), network computer, set top box, game player, mobile device, wireless device, wireless telephone, smartphone, personal digital assistant, media (e.g., music and/or video) player, camera, information appliance, workstation, minicomputer, mainframe computer, or any other device with computing functionality. A general purpose computer or a special purpose hardware device may be utilized.

A communications network may be used to connect components of the system 10. The communication may take place via any media such as standard telephone lines, cell phone networks, LAN or WAN links (e.g., T1, T3, 56 kb, X.25), broadband connections (ISDN, Frame Relay, ATM), wireless links (802.11, Bluetooth, cellular, etc.), and so on, in any suitable combination. Non-limiting examples of networks that can serve as or be part of the communications network include a wireless or wired Ethernet-based intranet, a local or wide-area network (LAN or WAN), and/or the global communications network known as the Internet, which may accommodate many different communications media and protocols.

Those skilled in the art will appreciate that various implementations of the invention may be practiced with various computer system configurations, including handheld wireless devices such as mobile phones or personal digital assistants (PDAs), multiprocessor systems, microprocessor-based or programmable consumer electronics, minicomputers, mainframe computers, and the like.

The invention may also be practiced in distributed computing environments where tasks are performed by remote processing devices that are linked through a communications network. In a distributed computing environment, program modules may be located in both local and remote computer storage media including memory storage devices.

In some cases, relational (or other structured) databases may provide data storage and management functionality, for example as a database management system or a database server which stores data (e.g., care plans and/or decision trees) related to the services and consumers utilizing the service. Examples of databases include the MySQL Database Server or ORACLE Database Server offered by ORACLE Corp. of Redwood Shores, Calif., the PostgreSQL Database Server by the PostgreSQL Global Development Group of Berkeley, Calif., or the DB2 Database Server offered by IBM.

Computers typically include a variety of computer readable media that can form part of a system memory and be read by a processing unit. By way of example, and not limitation, computer readable media may include computer storage media and communication media. The system memory may include computer storage media in the form of volatile and/or nonvolatile memory such as read only memory (ROM) and random access memory (RAM). A basic input/output system (BIOS), containing the basic routines that help to transfer information between elements, such as during start-up, is typically stored in ROM. RAM typically contains data and/or program modules that are immediately accessible to and/or presently being operated on by processing unit. The data or program modules may include an operating system, application programs, other program modules, and program data. The operating system may be or include a variety of operating systems such as Microsoft Windows® operating system, the Unix operating system, the Linux operating system, the Xenix operating system, the IBM AIX™ operating system, the Hewlett Packard UX™ operating system, the Novell Netware™ operating system, the Sun Microsystems Solaris™ operating system, the OS/2™ operating system, or another operating system of platform.

At a minimum, the memory includes at least one set of instructions that is either permanently or temporarily stored. The processor executes the instructions that are stored in order to process data. The set of instructions may include various instructions that perform a particular task or tasks. Such a set of instructions for performing a particular task may be characterized as a program, software program, software, engine, module, component, mechanism, or tool.

The system 10 may include a plurality of software processing modules stored in a memory as described above and executed on the computer. The program modules may be in the form of any suitable programming language, which is converted to machine language or object code to allow the processor or processors to read the instructions. That is, written lines of programming code or source code, in a particular programming language, may be converted to machine language using a compiler, assembler, or interpreter. The machine language may be binary coded machine instructions specific to a particular computer.

Any suitable programming language may be used in accordance with the various embodiments of the invention. Illustratively, the programming language used may include assembly language, Ada, APL, Basic, C, C++, COBOL, dBase, Forth, FORTRAN, Java, Modula-2, Pascal, Prolog, REXX, and/or JavaScript, for example. Further, it is not necessary that a single type of instruction or programming language be utilized in conjunction with the operation of the system and method of the invention. Rather, any number of different programming languages may be utilized as is necessary or desirable.

The computing environment may also include other removable/non-removable, volatile/nonvolatile computer storage media. For example, a hard disk drive may read or write to non-removable, nonvolatile magnetic media. A magnetic disk drive may read from or writes to a removable, nonvolatile magnetic disk, and an optical disk drive may read from or write to a removable, nonvolatile optical disk such as a CD-ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The storage media are typically connected to the system bus through a removable or non-removable memory interface.

The processing unit that executes commands and instructions may be a general purpose computer, but may utilize any of a wide variety of other technologies including a special purpose computer, a microcomputer, mini-computer, mainframe computer, programmed micro-processor, microcontroller, peripheral integrated circuit element, a CSIC (Customer Specific Integrated Circuit), ASIC (Application Specific Integrated Circuit), a logic circuit, a digital signal processor, a programmable logic device such as an FPGA (Field Programmable Gate Array), PLD (Programmable Logic Device), PLA (Programmable Logic Array), RFID integrated circuits, smart chip, or any other device or arrangement of devices that is capable of implementing the steps of the processes of the invention.

It should be appreciated that the processors and/or memories of the computer system need not be physically in the same location. Each of the processors and each of the memories used by the computer system may be in geographically distinct locations and be connected so as to communicate with each other in any suitable manner via, for example, a communications interface. Additionally, it is appreciated that each of the processor and/or memory may be composed of different physical pieces of equipment.

A user may enter commands and information into the computer through one or more user device interfaces that communicate with input devices such as a keyboard and pointing device, commonly referred to as a mouse, trackball or touch pad. Other input devices may include a microphone, joystick, game pad, satellite dish, scanner, voice recognition device, keyboard, touch screen, toggle switch, pushbutton, or the like. These and other input devices are often connected to the processing unit through a user input interface that is coupled to the system bus, but may be connected by other interface and bus structures, such as a parallel port, game port or a universal serial bus (USB).

One or more monitors or display devices (not shown) may also be connected to the system bus via an interface. In addition to display devices, computers may also include other peripheral output devices, which may be connected through an output peripheral interface. The computers implementing the invention may operate in a networked environment using logical connections to one or more remote computers, the remote computers typically including many or all of the elements described above.

Although internal components of the computer are not shown, those of ordinary skill in the art will appreciate that such components and the interconnections are well known. Accordingly, additional details concerning the internal construction of the computer need not be disclosed in connection with the present invention.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A computer-implemented method of evaluating treatment parameters for a patient undergoing radiotherapy, wherein a portal imaging device is located under the patient such that a radiation beam passes through the patient to the portal imaging device, the method comprising:
   obtaining, from an initial medical imaging device, a planning image of the patient prior to radiotherapy, the planning image including an expected portal image of a target region of the patient;
   obtaining a portal image during radiotherapy from the portal imaging device, the portal image corresponding to an actual dose distribution delivered to the target region of the patient when a radiation beam is turned on;
   generating, by a processor of a portal dosimetry system, during radiotherapy, a first portal dosimetry image identifying one or more differences between the planning image and the portal image;
   accessing, over an electronic communications network, a database configured to store a plurality of prior portal dosimetry images identifying:
      differences between prior planning images and prior portal images;
      assessment information for the prior portal dosimetry images, the assessment information including at least one of true positive difference information and false positive difference information; and
      one or more corresponding decisions made regarding the prior portal dosimetry images;
   performing a similarity measurement, by the processor, between the first portal dosimetry image and the prior portal dosimetry images from the database;
   determining, by the processor, whether to interrupt radiotherapy, wherein the determination is based on an analysis of the similarity measurement, the assessment information, and the corresponding decisions made regarding the prior portal dosimetry images; and
   providing, by the processor, an indication of whether to interrupt radiotherapy, the indication being displayed on a graphical user interface of the portal dosimetry system.

2. The method of claim 1, wherein the processor further generates a ranked list of likely explanations for any differences seen in the difference portal dosimetry image based on the assessment information.

3. The method of claim 1, wherein the one or more corresponding decisions are related to at least one of: whether the patient is a different patient, whether the patient is outside of a predefined position, whether the radiation beam is being delivered to a location outside of a predefined region, whether a change in the patient's position is greater than a predefined threshold, or combinations thereof.

4. The method of claim 1, wherein the portal image comprises a 3D image reconstructed from a plurality of 2D images of the target region obtained during radiotherapy.

5. The method of claim 1, wherein the planning image comprises a 3D image that includes a plurality of predicted 2D images of the target region.

6. The method of claim 1, wherein the similarity measurement is performed between the first portal dosimetry image and the prior portal dosimetry images for the same patient from previous treatment sessions.

7. The method of claim 1, wherein the processor further determines a gamma index based on differences between the planning image and the portal image, wherein a gamma test is failed if the gamma index exceeds a threshold value.

8. The method of claim 1, wherein the interruption of radiotherapy includes making one or more changes to a treatment plan.

9. A portal dosimetry system for evaluating treatment parameters for a patient undergoing radiotherapy, the system comprising:
   a database storing a plurality of prior portal dosimetry images, wherein each prior portal dosimetry image includes:
      differences between a prior planning image and a prior portal image;

assessment information for the prior portal dosimetry image, the assessment information including at least one of true positive difference information and false positive difference information; and one or more corresponding decisions made regarding the prior portal dosimetry image;

an initial medical imaging device configured for obtaining a planning image including an expected portal image of a target region of the patient;

a portal imaging device located under the patient such that a radiation beam passes through the patient to the portal imaging device, wherein the portal imaging device is configured to take a portal image corresponding to an actual dose distribution delivered to the target region of the patient when a radiation beam is turned on during radiotherapy;

a display configured to display a graphical user interface; and a processor configured to:

generate, during radiotherapy, a first portal dosimetry image identifying one or more differences between the planning image and the portal image;

access, over an electronic communications network, the database;

perform a similarity measurement between the portal dosimetry image and the prior portal dosimetry images from the database;

determine whether to interrupt radiotherapy, wherein the determination is based on an analysis of the similarity measurement, the assessment information, and the corresponding decisions made regarding the one or more prior portal dosimetry images; and provide an indication of whether to interrupt radiotherapy to the display.

10. The system of claim 9, wherein the processor is further configured to generate a ranked list of likely explanations for any differences seen in the first portal dosimetry image based on the assessment information.

11. The system of claim 9, wherein the one or more corresponding decisions are related to at least one of: whether the patient is a different patient, whether the patient is outside of a predefined position, whether the radiation beam is being delivered to a location outside of a predefined region, whether a change in the patient's position is greater than a predefined threshold, or combinations thereof.

12. The system of claim 9, wherein the portal image comprises a 3D image reconstructed from a plurality of 2D images of the target region obtained during radiotherapy.

13. The system of claim 9, wherein the planning image comprises a 3D image that includes a plurality of predicted 2D images of the target region.

14. The system of claim 9, wherein the similarity measurement is performed between the portal dosimetry image and the prior portal dosimetry images for the same patient from previous treatment sessions.

15. The system of claim 9, wherein the processor is further configured to determine a gamma index based on differences between the planning image and the portal image, wherein a gamma test is failed if the gamma index exceeds a threshold value.

16. The system of claim 9, wherein the interruption of radiotherapy includes making one or more changes to a treatment plan.

17. A system for evaluating treatment parameters for a patient undergoing radiotherapy using a portal imaging device located under the patient such that a radiation beam passes through the patient to the portal imaging device when a radiation beam is turned on during radiotherapy, wherein the portal imaging device is configured to take a portal image corresponding to an actual dose distribution delivered to a target region of the patient when a radiation beam is turned on during radiotherapy, the system comprising:

a database storing a plurality of prior portal dosimetry images, wherein each prior portal dosimetry image includes:

differences between a prior planning image and a prior portal image;

assessment information for the prior portal dosimetry image, the assessment information including at least one of true positive difference information and false positive difference information; and one or more corresponding decisions made regarding the prior portal dosimetry image;

an initial medical imaging device configured for obtaining a planning image including an expected portal image of the target region of the patient; and a graphical display configured to provide an indication of whether to interrupt radiotherapy based on a difference between the planning image and the portal image.

18. The system of claim 17, further comprising:

a processor configured to:

generate, during radiotherapy, a portal dosimetry image identifying one or more differences between the planning image and the portal image;

access, over an electronic communications network, the database;

perform a similarity measurement between the portal dosimetry image and the prior portal dosimetry images from the database; and determine whether to interrupt radiotherapy, wherein the determination is based on an analysis of the similarity measurement, the assessment information, and the corresponding decisions made regarding the one or more prior portal dosimetry images.

19. The system of claim 18, wherein the processor further generates a ranked list of likely explanations for any differences seen in the first portal dosimetry image based on the assessment information.

20. The system of claim 18, wherein the one or more corresponding decisions are related to at least one of: whether the patient is a different patient, whether the patient is outside of a predefined position, whether the radiation beam is being delivered to a location outside of a predefined region, whether a change in the patient's position is greater than a predefined threshold, or combinations thereof.

21. The system of claim 18, wherein the portal image comprises a 3D image reconstructed from a plurality of 2D images of the target region obtained during radiotherapy.

22. The system of claim 18, wherein the planning image comprises a 3D image that includes a plurality of predicted 2D images of the target region.

23. The system of claim 18, wherein the similarity measurement is performed between the first portal dosimetry image and the prior portal dosimetry images for the same patient from previous treatment sessions.

24. The system of claim 18, further comprising the processor determining a gamma index based on differences between the planning image and the portal image, wherein a gamma test is failed if the gamma index exceeds a threshold value.

25. The system of claim 18, wherein the interruption of radiotherapy includes making one or more changes to a treatment plan.

* * * * *